(12) United States Patent
Ishibashi et al.

(10) Patent No.: US 10,426,783 B2
(45) Date of Patent: Oct. 1, 2019

(54) THERAPEUTIC AGENT FOR OCULAR FUNDUS DISEASE

(71) Applicants: KYUSHU UNIVERSITY, NATIONAL UNIVERSITY CORPORATION, Fukuoka-Shi, Fukuoka (JP); KOWA COMPANY, LTD., Nagoya-Shi, Aichi (JP)

(72) Inventors: Tatsuro Ishibashi, Fukuoka (JP); Shintaro Nakao, Fukuoka (JP); Ryoichi Arita, Fukuoka (JP); Ken Mizuno, Higashimurayama (JP); Akifumi Tsuchiura, Tokyo (JP)

(73) Assignees: KYUSHU UNIVERSITY, NAT'L UNIVERSITY CORPORATION, Fukuoka-shi (JP); KOWA COMPANY, LTD., Nagoya-shi (JP)

( * ) Notice: Subject to any disclaimer, the term of this patent is extended or adjusted under 35 U.S.C. 154(b) by 0 days.

(21) Appl. No.: 15/387,113

(22) Filed: Dec. 21, 2016

(65) Prior Publication Data

US 2017/0100409 A1   Apr. 13, 2017

Related U.S. Application Data

(63) Continuation of application No. 14/362,850, filed as application No. PCT/JP2014/001123 on Mar. 3, 2014.

(30) Foreign Application Priority Data

Apr. 24, 2013 (JP) ................. 2013-090851

(51) Int. Cl.
 *A61K 31/551* (2006.01)
 *A61K 9/00* (2006.01)
 *A61K 31/496* (2006.01)
 *C07D 401/12* (2006.01)
 *A61K 47/10* (2017.01)

(52) U.S. Cl.
 CPC .......... *A61K 31/551* (2013.01); *A61K 9/0046* (2013.01); *A61K 9/0048* (2013.01); *A61K 31/496* (2013.01); *C07D 401/12* (2013.01); *A61K 47/10* (2013.01)

(58) Field of Classification Search
 CPC ... A61K 31/551; A61K 9/0048; C07D 401/12
 See application file for complete search history.

(56) References Cited

U.S. PATENT DOCUMENTS

| | | | |
|---|---|---|---|
| 2004/0106646 A1 | 6/2004 | Takayama et al. | |
| 2006/0142270 A1* | 6/2006 | Sugimoto | A61K 31/55 514/218 |
| 2008/0194584 A1 | 8/2008 | Birault et al. | |
| 2011/0144150 A1 | 6/2011 | Lampe et al. | |

FOREIGN PATENT DOCUMENTS

| | | |
|---|---|---|
| CN | 101087613 A | 12/2007 |
| EP | 0956865 A1 | 11/1999 |
| EP | 1818059 A1 | 8/2007 |
| JP | 11-349482 A | 12/1999 |
| JP | 2006-290827 A | 10/2006 |
| JP | 2007-084474 A | 4/2007 |
| JP | 2007-182438 A | 7/2007 |
| JP | 2008-519814 A | 6/2008 |
| JP | 2013-513664 A | 4/2013 |
| WO | 98/06433 A1 | 2/1998 |
| WO | 99/20620 A1 | 4/1999 |
| WO | 02/083175 A1 | 10/2002 |
| WO | 2004/106325 A1 | 12/2004 |
| WO | 2006/068208 A1 | 6/2006 |
| WO | 2011/149012 A1 | 12/2011 |
| WO | 2012/012282 A1 | 1/2012 |
| WO | 2012/015760 A1 | 2/2012 |

OTHER PUBLICATIONS

Zandi et al, Investigative Ophthalmology & Visual Science, April, vol. 50, 784. (Year: 2009).*
Liu et al, BMJ Open, 3: e004146, 1-7 (Year: 2014).*
Patani et al, Chem.Rev., 96, 3147-3176 (Year: 1996).*
Kita, Takeshi, "Molecular Mechanism of Preretinal Membrane Contraction in Proliferative Vitreoretinal Disease and ROCK as a Therapeutic Target", Journal of Japanese Ophthalmological Society, Nov. 10, 2010, vol. 114, No. 11, pp. 927-934, cited in ISR.
Kita, Takeshi, et al., "Role of TGF-b in proliferative vitreoretinal diseases and ROCK as a therapeutic target", PNAS, Nov. 11, 2008, vol. 105, No. 45, pp. 17504-17509.
Hata, Yasuaki, "Preventive Strategy for the Treatment of Diabetic Vitreoretinopathy", Journal of Japanese Ophthalmological Society, Mar. 10, 2009, vol. 113, No. 3, pp. 379-402.
Arita, Ryoichi, "Mechanism of Diabetes-Induced Microvascular Damage and Therapeutic potential of ROCK Inhibition", Journal of Japanese Ophthalmological Society, Nov. 10, 2011, vol. 115, No. 11, pp. 985-997.
Arita, Ryoichi, et al., "Rho Kinase Inhibition by Fasudil Ameliorates Diabetes-Induced Microvascular Damage", Diabetes, vol. 58, Jan. 2009, pp. 215-226.
Arita, Ryoichi, "Clinical applicability of ROCK inhibitors to diabetic retinopathy", Friday-SP7-4, The 67th Annual Congress of Japan Clinical Ophthalmology, Sep. 20, 2013, with partial English translation.
Yokota, Tamotsu, et al., "Involvement of the Rho/Rho Kinase Signaling Pathway in Platelet-Derived Growth Factor BB-induced Vascular Endothelial Growth Factor Expression in Diabetic Rat Retina", Japanese Journal of Ophthalmology, 2007, vol. 51, No. 6, pp. 424-430, cited in ISR.

(Continued)

*Primary Examiner* — Sudhakar Katakam
(74) *Attorney, Agent, or Firm* — Westerman, Hattori, Daniels & Adrian, LLP

(57) ABSTRACT

Disclosed herein is a prophylactic or therapeutic agent for ocular fundus disease, especially diabetic retinopathy or age-related macular degeneration. The prophylactic or therapeutic agent for ocular fundus disease comprising: (S)-(−)-1-(4-fluoro-5-isoquinolinesulfonyl)-2-methyl-1,4-homopiperazine, a salt thereof, or a solvate thereof, as an active ingredient.

7 Claims, 13 Drawing Sheets

(56) References Cited

OTHER PUBLICATIONS

Nakao, Shintaro, "ROCK in Diabetic Retinopathy: Clinical Application of Topical ROCK Inhibitor", S2-3, Journal of Japanese Ophthalmological Society, Mar. 3, 2014, vol. 118, with partial English translation (10 pages).
Nakao, Shintaro, "Diabetic Retinopathy", Journal of Eye, vol. 29 (Suppl.), 2012, pp. 60-67, cited in specification.
Yin, Limei et al., "Fasudil inhibits vascular endothelial growth factor-induced angiogenesis in vitro and in vivo", Molecular Cancer Therapeutics, 2007, No. 6, May 18, 2007, pp. 1517-1525, cited in specification.
Bryan, Brad et al., "RhoA/ROCK signaling is essential for multiple aspects of VEGF-mediated angiogenesis", The FASEB Journal, vol. 24, Sep. 2010, pp. 3186-3195, cited in specification.
Fang, Xiaoyun, et al., "RhoA Activation and Effect of Rho-kinase Inhibitor in the Development of Retinal Neovascularization in a Mouse Model of Oxygen-induced Retinopathy", Current Eye Research, 36(11), 2011, pp. 1028-1036, cited in specification.
Kawahara, Shuhei, et al., "Potent Inhibition of Cicatricial Contraction on Proliferative Vitreoretinal Disease by Statins", Diabetes, vol. 57, Oct. 2008, pp. 2784-2793.
"IyakuSearch", JAPIC Clinical Trials Information, http://www.clinicaltrials.jp/user/cteDetail_e.jsp, dated Feb. 27, 2014; 3 pages.
International Search Report dated May 20, 2014, issued in corresponding International Patent Application PCT/JP2014/001123, with English translation (10 pages).
Written Opinion dated May 20, 2014, issued in corresponding International Patent Application No. PCT/JP2014/001123, with English translation (12 pages).
Notification of Reasons for Refusal dated Apr. 22, 2014, issued in corresponding Japanese Patent Application No. 2014-040041, with English translation (4 pages).
Liu, Lei, et al., "Prevalence of ocular fundus pathology with type 2 diabetes in a Chinese urban community as assessed by telescreening" Dec. 1, 2013, BMJ Open, vol. 3, No. 12, pp. 1-8; cited in Supplementary European Search Report dated Nov. 29, 2016.
Partial Supplementary European Search Report dated Nov. 29, 2016, issued in counterpart European Patent Application No. 14788679.0. (7 pages).
Zandi, S, et al., ROCK Inhibition by Fasudil Suppresses Choroidal Neovascularization, Apr. 2009, Investigative Ophthalmology & Visual Science, Meeting Abstracts, vol. 50, p. 784.
National Eye Institute, Facts about Diabetic Eye Disease, Sep. 2015, https://nei.nih.gov/health/diabetic/retinopathy.
Extended (supplementary) European Search Report dated Jun. 7, 2017, issued in counterpart to European Patent Application No. 14788679.0. (14 pages).
Office Action dated Jan. 3, 2017, issued in counterpart Chinese Application No. 201480013090.6. (5 pages).

* cited by examiner

Saline 0.4% Compound 1

0.8% Compound 1

Saline

Fasudil 0.4%

Saline 0.8 % Compound 1

0.8% Compound 1

Saline

Normal mouse (Reference)

THERAPEUTIC AGENT FOR OCULAR FUNDUS DISEASE

CROSS-REFERENCE TO RELATED APPLICATIONS

This is a continuation of U.S. patent application Ser. No. 14/362,850, filed on Jun. 4, 2014, which is a 371 of International Application No. PCT/JP2014/001123, filed on Mar. 3, 2014, which claims the benefit of priority from the prior Japanese Patent Application No. 2013-090851, filed on Apr. 24, 2013, the entire contents of which are incorporated herein by reference.

TECHNICAL FIELD

The present invention relates to a drug for preventing or treating ocular fundus disease, especially diabetic retinopathy or age-related macular degeneration.

BACKGROUND ART

Diabetic retinopathy (DR, also referred to as diabetic retinal disease) is one of the three major complications of diabetes, the others being diabetic nephropathy and diabetic neuropathy, and is the second leading cause of blindness in adults after glaucoma in Japan. If blood glucose remains at a high level, small blood vessels in the retina are gradually damaged and then deformed or blocked. As a result of such so-called hyperglycemic microangiopathy, oxygen does not reach every corner of the retina so that the retina becomes hypoxia. As a result, new blood vessels (neovascular vessels) are formed to compensate for the lack of oxygen. However, neovascular vessels are fragile, and therefore bleeding easily occurs so that a scab-like membrane (proliferative membrane) is formed on the retina, which may be the cause of retinal detachment (proliferative diabetic retinopathy).

Diabetic retinopathy is broadly classified into three stages, simple diabetic retinopathy, preproliferative diabetic retinopathy, and proliferative diabetic retinopathy depending on the degree of progression. Even in the stage of simple diabetic retinopathy, maculopathy with macular edema or hard exudate (diabetic macular edema or diabetic maculopathy) may develop, which mainly results from increased vascular permeability. In either case, diagnosis based on ocular fundus findings is important.

It is known that diabetic macular edema develops regardless of the disease stage of diabetic retinopathy. Diabetic macular edema is a disease that is caused by accumulation of a plasma component leaked from retinal blood vessels due to increased vascular permeability in the macula and that is associated with a subjective symptom such as anorthopia or reduced visual acuity.

Simple diabetic retinopathy is sometimes improved by blood glucose control, but it is believed that in most cases, preproliferative diabetic retinopathy needs to be treated by retinal photocoagulation. When proliferative diabetic retinopathy develops so that retinal detachment or vitreous hemorrhage occurs, vitreous surgery is performed for the purpose of removing blood or grown tissue in the eye or reattaching the detached retina. However, at present, it is still not always possible to maintain good visual function.

Age-related macular degeneration (AMD) is a disease in which the macula is directly or indirectly damaged by waste products accumulated under the retinal pigment epithelium by aging. In Europe and the United States, age-related macular degeneration is the first leading cause of blindness in adults. Age-related macular degeneration is broadly classified into two types, atrophic (dry) type and exudative (wet) type. Atrophic AMD is a disease in which the retinal pigment epithelium becomes atrophic gradually so that the retina is damaged and therefore visual acuity is gradually reduced. At present, there is no known effective therapy for atrophic AMD. On the other hand, exudative AMD is a disease in which the retina is damaged by abnormal blood vessels (choroidal neovascular vessels) that extend from the choroid into the space under the retinal pigment epithelium or the space between the retina and the retinal pigment epithelium. Choroidal neovascular vessels cause accumulation of fluid (subretinal fluid) under the retina due to leakage of blood components or cause bleeding in the retina due to vascular disruption (retinal bleeding), and therefore the retina is damaged and does not properly function so that visual acuity is reduced.

There are some known therapies for exudative age-related macular degeneration. All the therapies are intended to suppress the choroidal neovascularization and regress the choroidal neovascular vessels to maintain or improve visual acuity. Examples of the known therapies for exudative age-related macular degeneration include photodynamic therapy (PDT), drug therapy, laser coagulation, and surgery. Among them, drug therapy is a therapeutic method in which a drug (VEGF inhibitor), whose action mechanism is to inhibit vascular endothelial growth factor (VEGF) considered to be largely concerned with the development of choroidal neovascularization, is injected into the vitreous body to regress choroidal neovascular vessels. However, as in the case of the treatment of diabetic retinopathy, it is still not always possible to maintain good visual acuity. Further, in the case of drug therapy, it is necessary to frequently administer the drug into the vitreous body.

Retinal neovascularization or choroidal neovascularization is largely responsible for the pathology of diabetic retinopathy or age-related macular degeneration, respectively, and therefore treatment intended to suppress or inhibit neovascularization has been tried. Treatment of age-related macular degeneration by intravitreal injection of the above-described VEGF inhibitor has already been covered by insurance in Japan, and clinical trials of the VEGF inhibitor for diabetic retinopathy are also in progress.

Further, as a target molecule different from VEGF, Rho-kinase (Rho-associated protein kinase: ROCK) has recently been received attention (Non-Patent Document 1). It is known that fasudil or Y-27632 known as a ROCK inhibitor has the effect of inhibiting VEGF-induced neovascularization (Non-Patent Documents 2 and 3). When intravitreally administered to diabetic model rats as model animals with retinal microangiopathy, fasudil has the effect of protecting endothelial cells due to suppression of adhesion of neutrophils to vascular endothelium or facilitation of the synthesis of nitrogen monoxide in endothelial cells, which suggests the potential of intravitreal administration of fasudil as a new treatment strategy for early-stage diabetic retinopathy (Non-Patent Documents 4 and 5). It is also shown that Y-27632 has the effect of suppressing retinal neovascularization when intravitreally administered to model mice with hyperoxia-induced retinopathy (Non-Patent Document 6). Some patent documents disclose that novel ROCK inhibitors can be used for treatment of retinopathy, diabetic retinopathy, macular degeneration, and the like, but in these patent documents, there is no description about the specific effect of the novel ROCK inhibitors on these diseases (Patent Documents 1 to 3).

As has been briefly described above, a drug intended to suppress chorioretinal neovascularization to treat diabetic retinopathy or age-related macular degeneration is mainly administered by intravitreal injection, but multiple injection into the human eye involves the risk of infection and imposes heavy physical, emotional, and financial burdens on patients. Therefore, development of therapy with an ophthalmic preparation has been desired.

Further, it is known that a 4-fluoro-5-cycloaminosufonyl isoquinoline derivative is effective as a therapeutic agent for asthma, a substance P antagonist, a leukotriene $D_4$ antagonist, and a Rho-kinase inhibitor (Patent Document 3) or as a therapeutic agent for cerebrovascular disorder (Patent Document 4), but there is no report about its selective action by local administration.

CITATION LIST

Patent Documents

Patent Document 1: WO 98/06433 A1
Patent Document 2: WO 02/083175 A1
Patent Document 3: JP H11-349482 A
Patent Document 4: WO 99/20620 A1

Non-Patent Documents

Non-Patent Document 1: Journal of the Eye, 29 (suppl.), 60-67 (2012)
Non-Patent Document 2: Mol. Cancer Ther., 6(5), 1517-1525 (2007)
Non-Patent Document 3: FASEB J., 24, 3186-3195 (2010)
Non-Patent Document 4: Diabetes, 58, 215-226 (2009)
Non-Patent Document 5: Journal of Japanese Ophthalmological Society, 115, 985-997
Non-Patent Document 6: Current Eye Research, 36(11), 1028-1036 (2011)

SUMMARY OF INVENTION

Problems to be Solved by the Invention

The present invention provides a novel drug for preventing or treating ocular fundus disease, especially diabetic retinopathy or age-related macular degeneration.

Means for Solving the Problems

The present inventors have intensively studied to solve the problems describe above, and have found that (S)-(−)-1-(4-fluoro-5-isoquinolinesulfonyl)-2-methyl-1,4-homopiperazine (hereinafter, sometimes referred to as "compound 1"), a salt thereof, or a solvate thereof surprisingly exerts a strong neovascularization suppression effect in the ocular fundus when administered by ocular instillation and that this compound is useful for preventing or treating ocular fundus disease, especially diabetic retinopathy or age-related macular degeneration, and thus have accomplished the present invention.

More specifically, the present invention includes the following aspects.

1) A prophylactic or therapeutic agent for ocular fundus disease comprising, as an active ingredient, (S)-(−)-1-(4-fluoro-54 soquinolinesulfonyl)-2-methyl-1,4-homopiperazine, a salt thereof, or a solvate thereof.

2) The prophylactic or therapeutic agent according to the above 1), wherein the ocular fundus disease is diabetic retinopathy.

3) The prophylactic or therapeutic agent according to the above 1), wherein the ocular fundus disease is diabetic macular edema.

4) The prophylactic or therapeutic agent according to the above 1), wherein the ocular fundus disease is age-related macular degeneration.

5) The prophylactic or therapeutic agent according to any of the above 1) to 4), which is an ophthalmic preparation.

6) A pharmaceutical composition for preventing or treating ocular fundus disease, comprising: (S)-(−)-1-(4-fluoro-54 soquinolinesulfonyl)-2-methyl-1,4-homopiperazine, a salt thereof, or a solvate thereof; and a pharmaceutically-acceptable carrier.

7) The pharmaceutical composition according to the above 6), wherein the ocular fundus disease is diabetic retinopathy.

8) The pharmaceutical composition according to the above 6), wherein the ocular fundus disease is diabetic macular edema.

9) The pharmaceutical composition according to the above 6), wherein the ocular fundus disease is age-related macular degeneration.

10) The pharmaceutical composition according to any of the above 6) to 9), which is an ophthalmic preparation.

11) A prophylactic or therapeutic method for ocular fundus disease comprising administering an effective amount of (S)-(−)-1-(4-fluoro-5-isoquinolinesulfonyl)-2-methyl-1,4-homopiperazine, a salt thereof, or a solvate thereof.

12) The prophylactic or therapeutic method according to the above 11), wherein the administration is performed by ocular instillation.

13) The prophylactic or therapeutic method according to the above 11) or 12), wherein the ocular fundus disease is diabetic retinopathy.

14) The prophylactic or therapeutic method according to the above 11) or 12), wherein the ocular fundus disease is diabetic macular edema.

15) The prophylactic or therapeutic method according to the above 11) or 12), wherein the ocular fundus disease is age-related macular degeneration.

16) An ophthalmic preparation comprising: (S)-(−)-1-(4-fluoro-5-isoquinolinesulfonyl)-2-methyl-1,4-homopiperazine, a salt thereof, or a solvate thereof; and a carrier acceptable to ophthalmic preparations.

17) Use of (S)-(−)-1-(4-fluoro-5-isoquinolinesulfonyl)-2-methyl-1,4-homopiperazine, a salt thereof, or a solvate thereof for production of a prophylactic or therapeutic agent for ocular fundus disease.

18) (S)-(−)-1-(4-fluoro-5-isoquinolinesulfonyl)-2-methyl-1,4-homopiperazine, a salt thereof, or a solvate thereof for use in a prophylactic or therapeutic agent for ocular fundus disease.

19) The use or compound according to the above 17) or 18), wherein the prophylactic or therapeutic agent for ocular fundus disease is an ophthalmic preparation.

20) The use or compound according to the above 17) or 18), wherein the ocular fundus disease is diabetic retinopathy.

21) The use or compound according to the above 17) or 18), wherein the ocular fundus disease is diabetic macular edema.

22) The use or compound according to the above 17) or 18), wherein the ocular fundus disease is age-related macular degeneration.

Effects of the Invention

According to the present invention, it is possible to provide a drug for preventing or treating ocular fundus disease, especially diabetic retinopathy or age-related macular degeneration.

The pharmaceutical composition, especially the ophthalmic preparation, according to the present invention is very useful as a therapeutic and/or prophylactic agent for ocular fundus disease because it is not only effective even at a low dose when administered by ocular instillation but also can be administered without imposing great physical and emotional burdens on patients, can be non-invasively administered, and can be easily administered also to elderly people and children.

Figure 1:
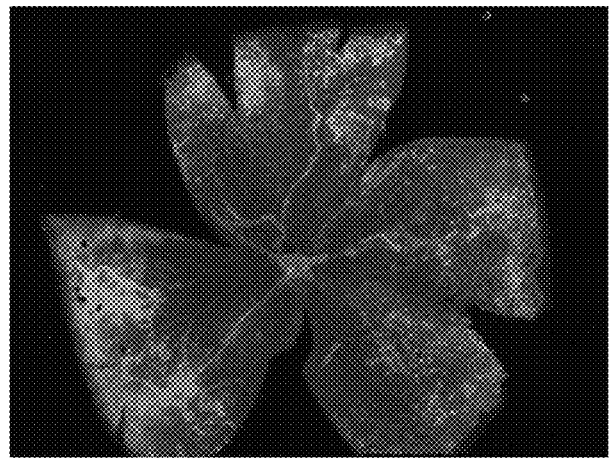
FIG. 1 shows the representative images of flat-mounted retinas of a saline instillation group (control), a 0.4% compound 1 solution instillation group, and a 0.8% compound 1 solution instillation group.
Figure 1:
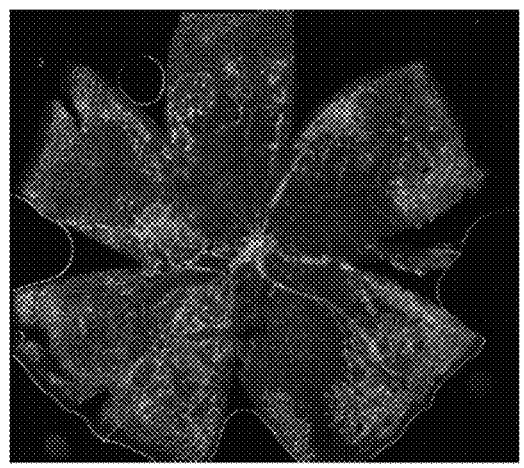
Figure 1:
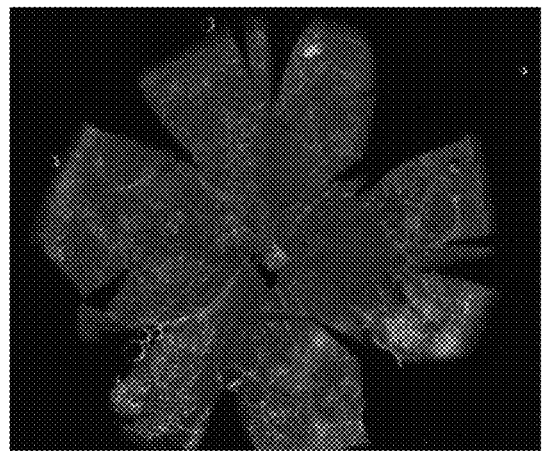

MODES FOR CARRYING OUT THE INVENTION (S)-(−)-1-(4-fluoro-5-isoquinolinesulfonyl)-2-methyl-1,4-homopiperazine used in the present invention is a compound that is effective as a therapeutic agent for cerebrovascular disease, has antagonistic actions on substance P and leukotriene $D_4$ and Rho kinase inhibition activity, and can be produced by a known method such as a method described in WO 99/20620 (Patent Document 4).

Examples of a salt of (S)-(−)-1-(4-fluoro-5-isoquinolinesulfonyl)-2-methyl-1,4-homopiperazine include: salts of inorganic acids such as hydrochloric acid, sulfuric acid, nitric acid, hydrofluoric acid, and hydrobromic acid; and salts of organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, and camphorsulfonic acid, and hydrochlorides are particularly preferred.

(S)-(−)-1-(4-fluoro-5-isoquinolinesulfonyl)-2-methyl-1,4-homopiperazine or a salt thereof can be present not only as an unsolvated form but also as a hydrate or a solvate. A hydrate is preferable as a solvate, but in the present invention, all forms of crystalline and hydrates and solvates of compound 1 are included as (S)-(−)-1-(4-fluoro-5-isoquinolinesulfonyl)-2-methyl-1,4-homopiperazine, a salt thereof, or a solvate thereof.

As will be described later with reference to examples, (S)-(−)-1-(4-fluoro-5-isoquinolinesulfonyl)-2-methyl-1,4-homopiperazine, a salt thereof, or a solvate thereof exerts a strong neovascularization suppression effect, and is therefore useful as a prophylactic or therapeutic agent for ocular fundus disease, especially diabetic retinopathy or age-related macular degeneration. Here, the ocular fundus disease mainly refers to a lesion that develops in the retina and/or choroid.

Examples of the ocular fundus disease include hypertensive or arteriosclerotic ocular fundus abnormalities, central retinal artery occlusion, retinal vein occlusion such as central retinal vein occlusion or branch retinal vein occlusion, diabetic retinopathy, diabetic macular edema, diabetic maculopathy, Eales disease, congenital retinal vascular abnormality such as Coats disease, von Hippel disease, pulseless disease, macular diseases (e.g. central serous chorioretinopathy, cystoid macular edema, age-related macular degeneration, macular hole, myopic macular degeneration, vitreoretinal interface maculopathy, drug-related maculopathy, and heredomacular degeneration), retinal detachment (e.g. rhegmatogenous, tractional, and exudative retinal detachment), retinitis pigmetosa, and retinopathy of prematurity.

A dosage form comprising (S)-(−)-1-(4-fluoro-5-isoquinolinesulfonyl)-2-methyl-1,4-homopiperazine, a salt thereof, or a solvate thereof can be prepared according to a known method. For example, a formulation comprising (S)-(−)-1-(4-fluoro-5-isoquinolinesulfonyl)-2-methyl-1,4-homopiperazine, a salt thereof, or a solvate thereof can be prepared with reference to dosage form examples described in, for example, WO 00/09162 or WO 97/23222.

A preparation comprising (S)-(−)-1-(4-fluoro-5-isoquinolinesulfonyl)-2-methyl-1,4-homopiperazine, a salt thereof, or a solvate thereof can also be prepared according to a known method. For example, an ophthalmic preparation can be prepared by using, if necessary, a tonicity agent, a buffering agent, a surfactant, a preservative, and the like. The pH of the ophthalmic preparation shall be within a range acceptable to ophthalmologic preparations, and is preferably in the range of 4 to 8.

The preparation according to the present invention is preferably used as an ophthalmologic preparation, especially as a preparation for ocular instillation. Such an ophthalmic preparation may be any one of an aqueous ophthalmic preparation, a non-aqueous ophthalmic preparation, an ophthalmic suspension, an ophthalmic emulsion, and an ophthalmic ointment. Such a dosage form suitable for administration can be produced by a (preparation) method known to those skilled in the art. If necessary, pharmaceutically-acceptable carriers, especially carriers acceptable to ophthalmic preparations, such as a tonicity agent, a chelating agent, a stabilizer, a pH adjuster, a preservative, an antioxidant, a solubilizing agent, a thickening agent, and the like can be added to the formulation.

The active ingredient used in the present invention is effective even at a low dose when administered by ocular instillation, and therefore can be used for ophthalmic preparations. An ophthalmic preparation according to the present invention comprises (S)-(−)-1-(4-fluoro-5-isoquinolinesulfonyl)-2-methyl-1,4-homopiperazine, a salt thereof, or a solvate thereof that is the active ingredient used in the present invention and a carrier acceptable to ophthalmic preparations.

The ophthalmic preparation can be prepared by, for example, dissolving or suspending desired ingredients such as the above-described ingredients in an aqueous solvent such as sterile purified water or saline or a non-aqueous solvent such as vegetable oil (e.g., cottonseed oil, soybean oil, sesame oil, or peanut oil) so that the osmotic pressure of the solution or suspension is adjusted to a predetermined value and then subjecting the solution or suspension to sterilization such as filtration sterilization. It is to be noted that when the ophthalmic ointment is prepared, an ointment base can be added in addition to the above-described various ingredients. Preferred examples of the ointment base include, but are not limited to: oily bases such as petrolatum, liquid paraffin, and polyethylene; emulsion bases obtained by emulsifying an oil phase and an aqueous phase with a surfactant; and water-soluble bases such as hydroxypropyl methylcellulose, carboxymethylcellulose, and polyethylene glycol.

When (S)-(−)-1-(4-fluoro-5-isoquinolinesulfonyl)-2-methyl-1,4-homopiperazine, a salt thereof, or a solvate thereof is used for preventing or treating ocular fundus disease, especially diabetic retinopathy or age-related macular degeneration, its dose varies depending on the body weight, age, sex, and symptom of a patient, the route and frequency of administration, and the like. Usually, the adult dose of (S)-(−)-1-(4-fluoro-5-isoquinolinesulfonyl)-2-methyl-1,4-homopiperazine, a salt thereof, or a solvate thereof is 0.025 to 10000 μg, preferably 0.025 to 2000 μg, more preferably 0.1 to 2000 μg per day. Further, the other preferable adult dose is 0.025 to 200 μs, or 0.025 to 100 μg per day.

The frequency of administration is not particularly limited, but the above daily dose is preferably administered once or in divided doses. In the case of a liquid ophthalmic preparation, one to several drops of the preparation shall be instilled into the eye at a time.

Hereinbelow, the present invention will be described in more detail, but is not limited to the following description.

EXAMPLES

Example 1

Effects in MICE OIR (Oxygen-Induced Retinopathy) Model

The effectiveness of (S)-(−)-1-(4-fluoro-5-isoquinolinesulfonyl)-2-methyl-1,4-homopiperazine (compound 1) in a mice OIR model commonly used as a model of ischemic retinopathy such as diabetic retinopathy was examined in the following manner.

1. Preparation of Test Compound Solutions

A. Preparation of Compound 1 Solution

A predetermined amount of (S)-(−)-1-(4-fluoro-5-isoquinolinesulfonyl)-2-methyl-1,4-homopiperazine monohydrochloride dihydrate and glycerin were dissolved in purified water, and then the pH of the solution was adjusted to 6.0 by adding sodium dihydrogen phosphate and sodium hydroxide to prepare a compound 1 solution having a desired concentration.

B. Preparation of Fasudil Solution

A fasudil solution having a desired concentration was prepared in the same manner as in the preparation of the above-described compound 1 solution except that a predetermined amount of fasudil dihydrochloride (LC Laboratories) was used instead of (S)-(−)-1-(4-fluoro-5-isoquinolinesulfonyl)-2-methyl-1,4-homopiperazine monohydrochloride dihydrate.

2. Test Method

A. Drugs and Animals Used in Test

Compound 1 solutions: 0.4% solution, 0.8% solution (instillation volume: 20 μL)

Fasudil solution: 0.4% solution (instillation volume: 20 μL)

Test animals: C57BL/6JJcl mice (sex: male, 8 to 14 mice per group)

B. Preparation of OIR Model, Drug Administration Method, and Evaluation Method

C57BL/6JJcl mice born on the same day were reared in a 75%-oxygen environment from day 7 after birth, and were then transferred to a normal indoor environment on day 12 after birth to start administration by ocular instillation. Test groups were a saline instillation group (control), a 0.4% compound 1 solution instillation group, a 0.8% compound 1 solution instillation group, and a 0.4% fasudil solution instillation group, and saline, the compound 1 solution, or the fasudil solution was administered by ocular instillation three times a day. On day 17 after birth, ischemic retinal areas (non-perfused areas) and neovascular areas were quantified for evaluation by flat-mounting or fluorescein fundus angiography. More specifically, 1 g/kg of pentobarbital (Nembutal) was administered intraperitoneally for euthanasia under deep anesthesia, and then both eyeballs were excised and fixed with 4% paraformaldehyde (PFA) at 37° C. for 1 hour, and the corneal limbus was circumferentially incised to remove the cornea and iris from the eyeball. Then, after fixation with 4% PFA at 37° C. for 1 hour, the lens, sclera, and choroid were removed, and the eye cup including the retina was isolated. Further, the retina was fixed with 4% PFA at 37° C. for 3 hours, washed with PBS three times (15 min per wash, 37° C.), dehydrated (methanol 50%→100%, 10 min per methanol treatment, 37° C.), washed with PBS three times (15 min per wash, 37° C.), and blocked with Blocking Buffer (1% BSA, 0.5% Triton-X in PBS) for 60 minutes (37° C.). Then, the retina was treated with a primary antibody (0.7% FITC-conjugates Anti-lectin Ab in PBS, 4° C., overnight) and washed with PBS three times (15 min per wash, 37° C.). Then, 4 to 6 cuts were radially made in the eye cup, and the flat-mounted retina was covered with Crystal Mount. Then, the image of the flat-mounted retina was taken with a fluorescence microscope (BZ-9000, KEYENCE Corp, Osaka, Japan), and the proportion of the non-perfused area to the entire retina and the proportion of the neovascular area to the entire retina were calculated by the following formulas in NIH image J software. The thus obtained values were converted to relative values by regarding the obtained values of the saline instillation group (control) as 100%, and statistical analysis was performed by Wilcoxon test.

Non-perfused area=area of avascular region/area of entire retina

Neovascular area=area of neovascular region/area of entire retina

In fluorescein fundus angiography, each of the animals was first given tropicamide by ocular instillation to cause mydriasis, anesthetized by intraperitoneal administration of 100 mg/kg of Ketalar and 10 mg/kg of Selactar, given 12 μL/g of a contrast agent for fluorescein fundus angiography by intraperitoneal injection, and subjected to imaging using Optos200TX (OPTOS PLC) to take a fluorescein fundus angiography image to calculate the proportion of a neovascular area to the entire retina by the above formula in NIH image J software. The thus obtained values were converted to relative values by regarding the obtained value of the saline instillation group (control) as 100%, and statistical analysis was performed by Wilcoxon test.

3. Results and Discussions

Figure 2:
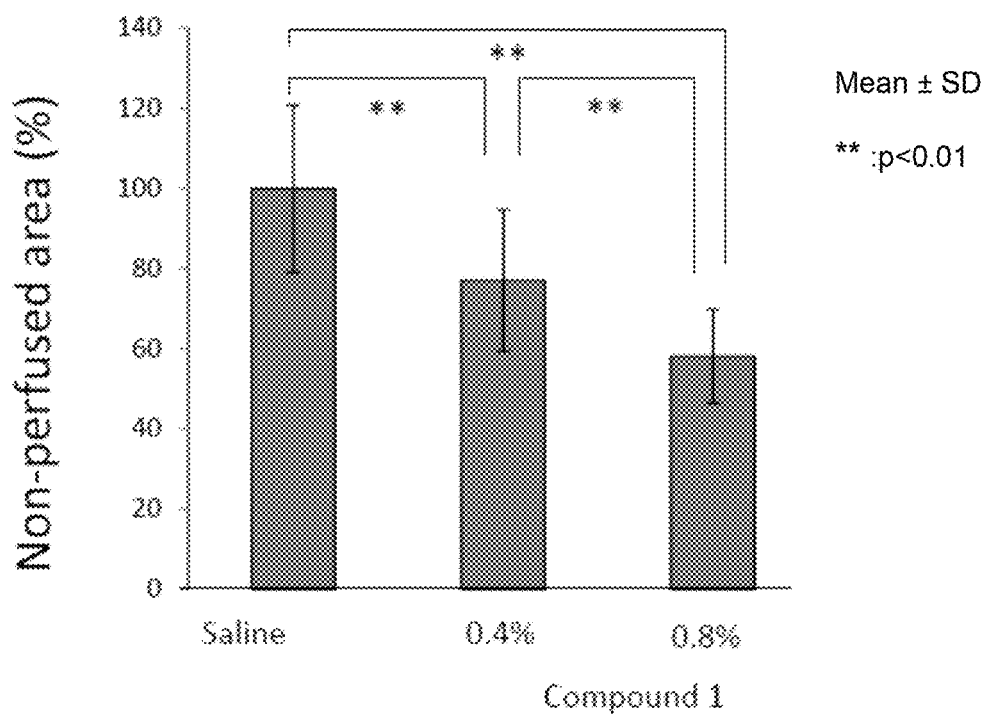
FIG. 2 is a graph showing the result of quantification of an ischemic retinal area (non-perfused area) in the flat-mounted retina of each of the instillation groups, wherein the vertical axis represents the relative value of the non-perfused area when the calculated proportion of non-perfused area of the saline instillation group is regarded as 100%, values are represented as mean±standard deviation, and ** indicates that p value is less than 0.01.
Figure 3:
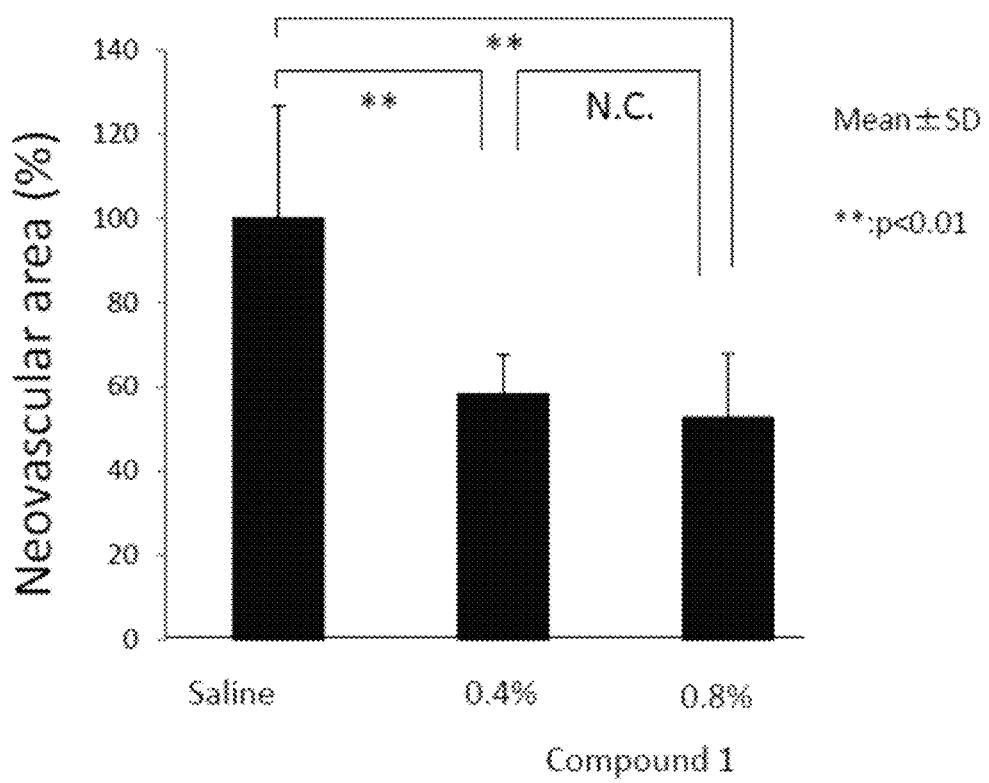
FIG. 3 is a graph showing the result of quantification of a neovascular area in the flat-mounted retina of each of the instillation groups, wherein the vertical axis represents the relative value of the neovascular area when the calculated proportion of neovascular area of the saline instillation group is regarded as 100%, values are represented as mean±standard deviation, ** indicates that p value is less than 0.01, and N.C. indicates that there is no significant difference.
Figure 4:
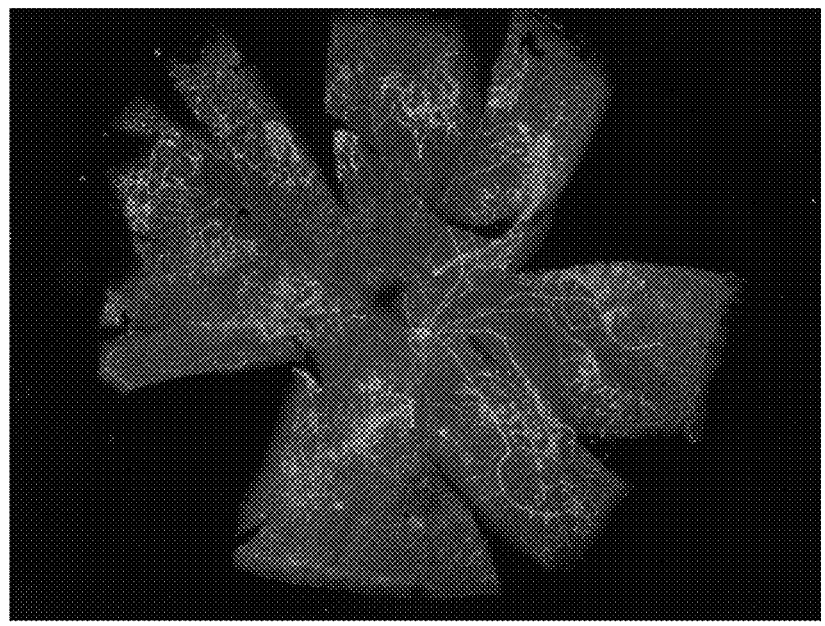
FIG. 4 shows representative images of flat-mounted retinas of a saline instillation group (control) and a 0.4% fasudil solution instillation group.
Figure 4:
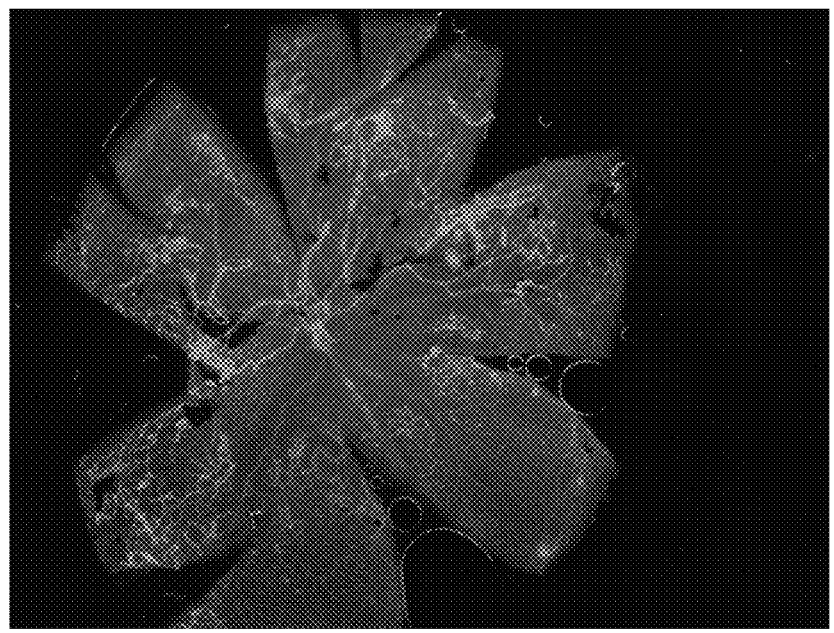
Figure 5:
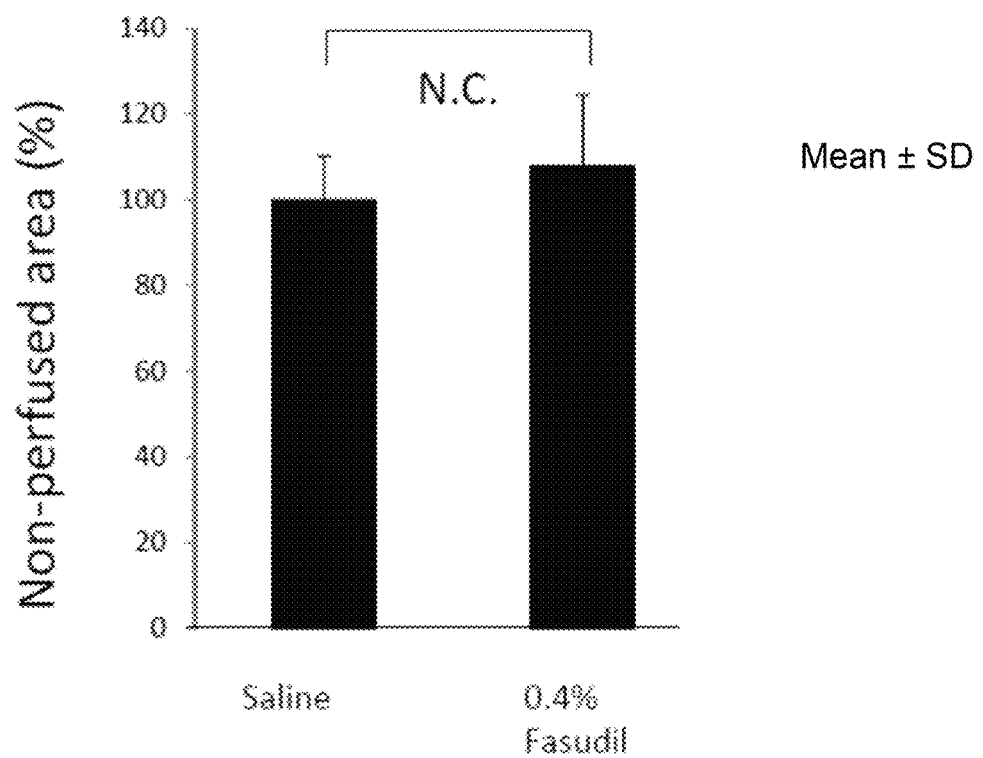
FIG. 5 is a graph showing the result of quantification of an ischemic retinal area (non-perfused area) in the flat-mounted retina of each of the saline instillation group (control) and the 0.4% fasudil solution instillation group, wherein the vertical axis represents the relative value of the non-perfused area when the calculated proportion of non-perfused area of the saline instillation group is regarded as 100%, values are represented as mean±standard deviation, and N.C. indicates that there is no significant difference.
Figure 6:
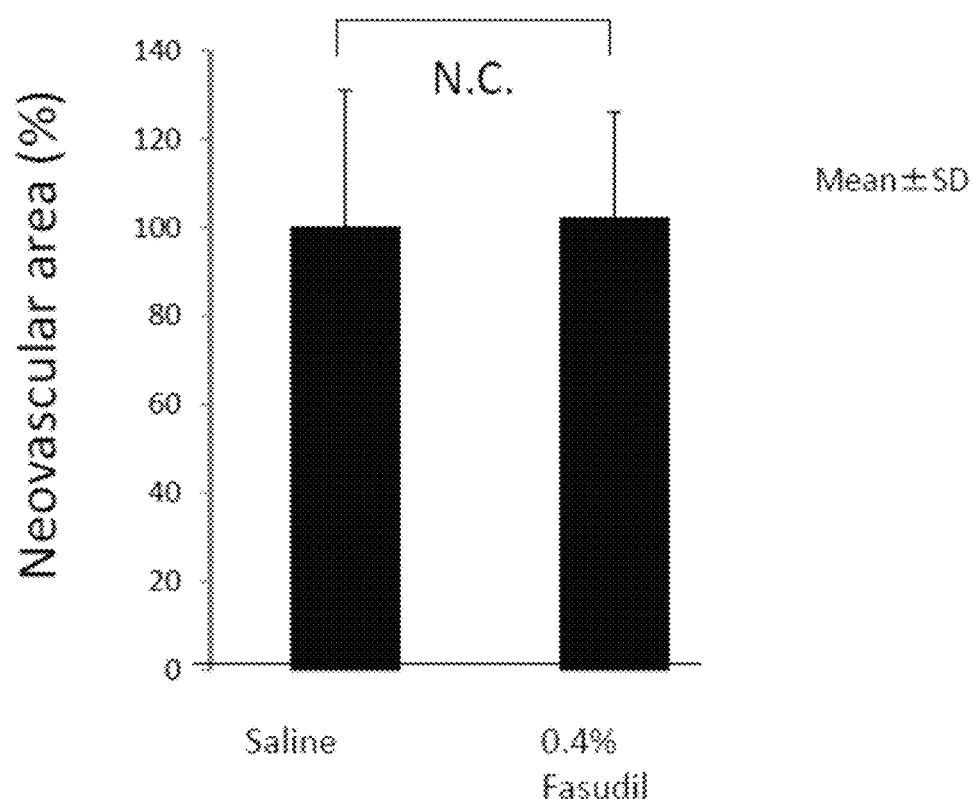
FIG. 6 is a graph showing the result of quantification of a neovascular area in the flat-mounted retina of each of the saline instillation group (control) and the 0.4% fasudil solution instillation group, wherein the vertical axis represents the relative value of the neovascular area when the calculated proportion of neovascular area of the saline instillation group is regarded as 100%, values are represented as mean±standard deviation, and N.C. indicates that there is no significant difference.

The results of ocular instillation of the compound 1 obtained by flat mounting are shown in FIGS. 1 to 3, and the results of ocular instillation of fasudil obtained by flat mounting are shown in FIGS. 4 to 6. FIG. 1 shows the representative images of flat-mounted retinas of the saline instillation group (control), the 0.4% compound 1 solution instillation group, and the 0.8% compound 1 solution instillation group. As can be seen from FIG. 1, the ischemic retinal area (non-perfused area) and the neovascular area are conspicuously observed in the saline instillation group, whereas suppression of the ischemic retinal area and the neovascularization is observed in both the 0.4% compound 1 solution instillation group and the 0.8% compound 1 solution instillation group. FIGS. 2 and 3 show the results of quantification of the ischemic retinal area (non-perfused area) and the neovascular area. As can be seen from FIG. 2, when the calculated proportion of non-perfused area of the saline instillation group (N=14) was regarded as 100%, the relative value of the non-perfused area of the 0.4% compound 1 solution instillation group (N=12) was 77.0% and the relative value of the non-perfused area of the 0.8% compound 1 solution instillation group (N=11) was 58.1%, that is, the non-perfused area was dose-dependently and significantly suppressed. Further, as can be seen from FIG. 3, when the calculated proportion of neovascular area of the saline instillation group was regarded as 100%, the relative value of the neovascular area of the 0.4% compound 1 solution instillation group was 58.2% and the relative value of the neovascular area of the 0.8% compound 1 solution instillation group was 52.7%, that is, the neovascular area was significantly suppressed.

On the other hand, FIG. 4 shows the representative images of flat-mounted retinas of the saline instillation group (control) and the 0.4% fasudil solution instillation group. As can be seen from FIG. 4, the ischemic retinal area (non-perfused area) and the neovascular area are conspicuously observed in both the groups. FIGS. 5 and 6 show the results of quantification of the ischemic retinal area (non-perfused area) and the neovascular area. As can be seen from FIG. 5, when the calculated proportion of non-perfused area of the saline instillation group (N=14) was regarded as 100%, the relative value of the non-perfused area of the 0.4% fasudil solution instillation group (N=13) was 107.7%, that is, the non-perfused area was not changed. Further, as can be seen from FIG. 6, when the calculated proportion of neovascular area of the saline instillation group was regarded as 100%, the relative value of the neovascular area of the 0.4% fasudil solution instillation group was 102.2%, that is, the neovascular area was not changed, either. Non-Patent Documents 5 discloses that fasudil is effective when injected into the vitreous body, but the effect of ocular instillation of fasudil could not be confirmed in the present invention.

Figure 7:
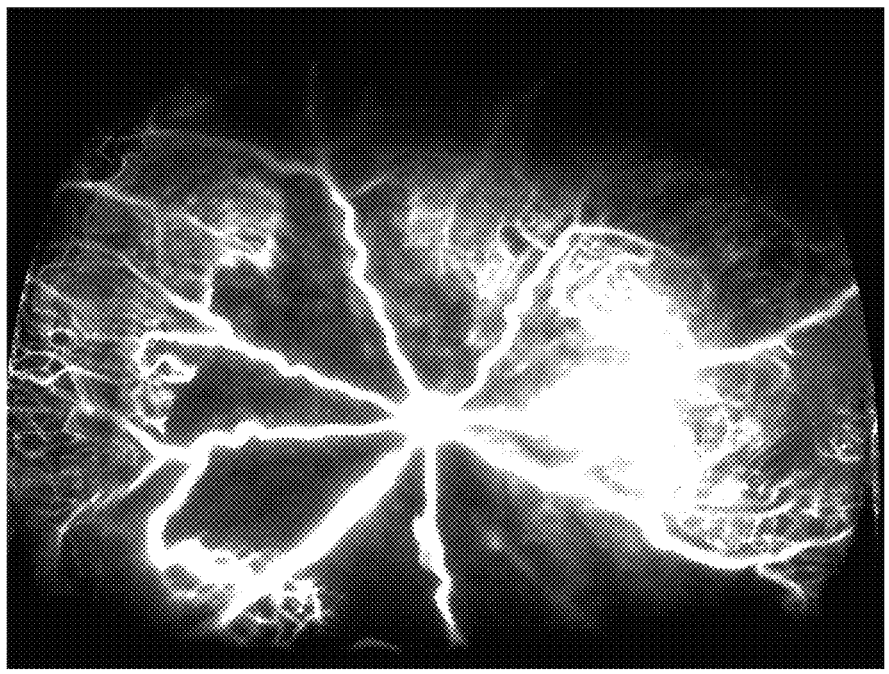
FIG. 7 shows representative fluorescein fundus angiography images of a saline instillation group (control) and a 0.8% compound 1 solution instillation group.
Figure 7:
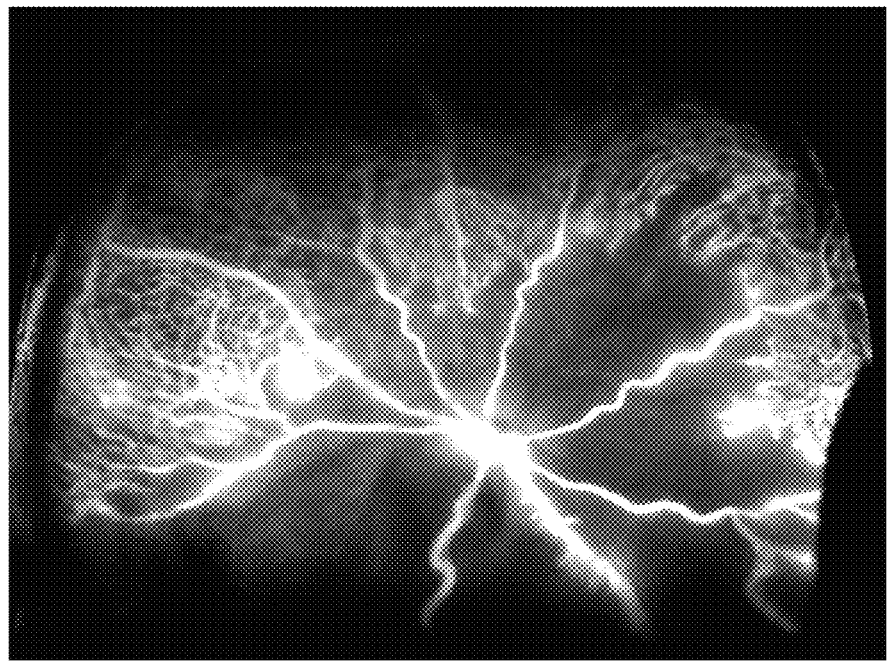
Figure 8:
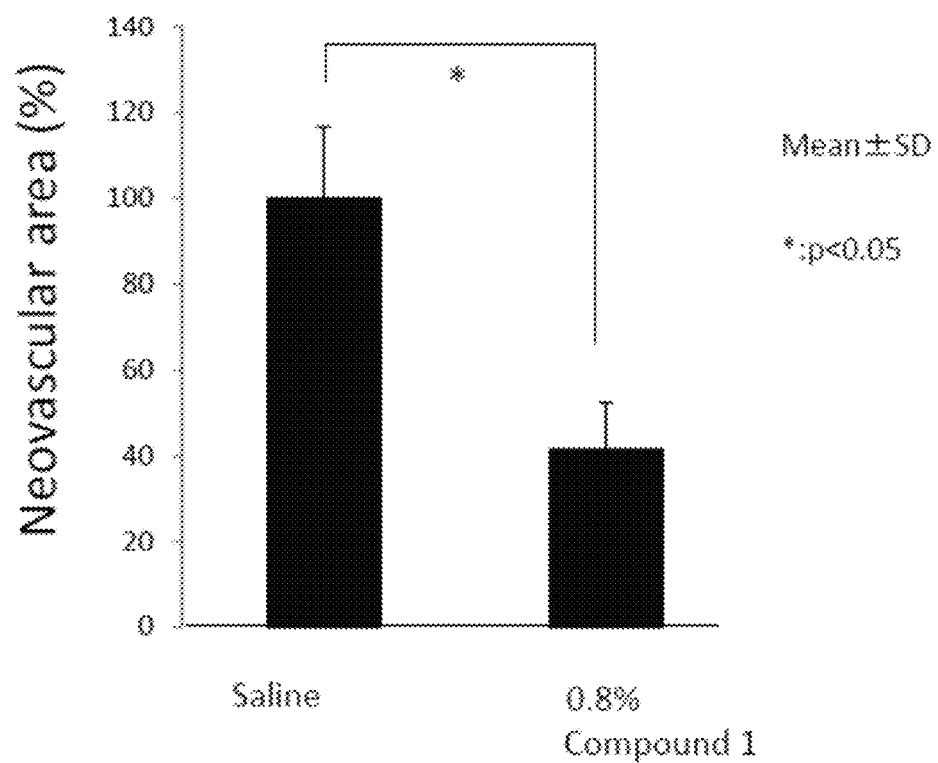
FIG. 8 is a graph showing the result of quantification of a neovascular area of each of the instillation groups by fluorescein fundus angiography, wherein the vertical axis represents the relative value of the neovascular area when the calculated proportion of neovascular area of the saline instillation group is regarded as 100%, values are represented as mean±standard error, and * indicates that p value is less than 0.05.

The results of fluorescein fundus angiography are shown in FIGS. 7 and 8. FIG. 7 shows the representative fluorescein fundus angiography images of the saline instillation group (control) and the 0.8% compound 1 solution instillation group. As can be seen from FIG. 7, the neovascular region is conspicuously observed in the saline instillation group, whereas suppression of the neovascular area is observed in the 0.8% compound 1 solution instillation group. FIG. 8 shows the results of quantification of the neovascular area. As can be seen from FIG. 8, when the calculated proportion of neovascular area of the saline instillation group (N=8) was regarded as 100%, the relative value of the neovascular area of the 0.8% compound 1 solution instillation group (N=8) was 41.6%, that is, the neovascular area was conspicuously and significantly suppressed.

The above results shown in FIGS. 1 to 3, FIG. 7, and FIG. 8 indicate that the development of the ischemic area and the neovascular area in the OIR model is conspicuously suppressed by ocular instillation of the compound 1. Further, the results shown in FIGS. 4 to 6 indicate that the effect obtained by the compound 1 cannot be obtained by fasudil.

Example 2

Effects in Mice CNV (Choroidal Neovascularization) Model

The effectiveness of the compound 1 in a mice CNV model known as a model of age-related macular degeneration or the like was examined in the following manner.

1. Test Method

A. Drugs and Animals Used in Test

Compound 1 solutions prepared in the same manner as in Example 1: 0.4% solution, 0.8% solution (instillation volume: 20 μL)

Test animals: C57BL/6JJcl mice (6- to 10-week old, sex: male, 11 to 12 mice per group)

B. Preparation of CNV Model, Drug Administration Method, and Evaluation Method

The preparation of a CNV model and evaluation were performed with reference to a literature (e.g., J. Leukoc. Biol. 2003; 74: 25-32, or Am. J. Pathol. 1998; 153: 1641-1646). More specifically, each of the mice was given tropicamide by ocular instillation to cause mydriasis, anesthetized by intraperitoneal administration of 100 mg/kg of Ketalar and 10 mg/kg of Selactar, and subjected to photocoagulation at 4 spots per eye. The photocoagulation was performed by krypton laser irradiation (75-μm spot size, 0.1 seconds duration, 200 mW) with a slit-lamp delivery system using a cover glass as a contact lens. Test groups were a saline instillation group (control), a 0.4% compound 1 solution instillation group, and a 0.8% compound 1 solution instillation group. Saline or the compound 1 solution was administered three times a day by ocular instillation. The day when photocoagulation treatment was performed was defined as day 0. Saline or the compound 1 solution was administered by ocular instillation from day 0 to day 7, a flat-mount was prepared on day 7, and blood vessels were stained with FITC-lectin for evaluation. More specifically, a spot with bleeding or tissue destruction was excluded, the CNV volume of each spot adopted was calculated by NIS-Elements AR Version 4.13, and then an average value ($\mu m^3$) per eye was calculated.

Results and Discussion

Figure 9:
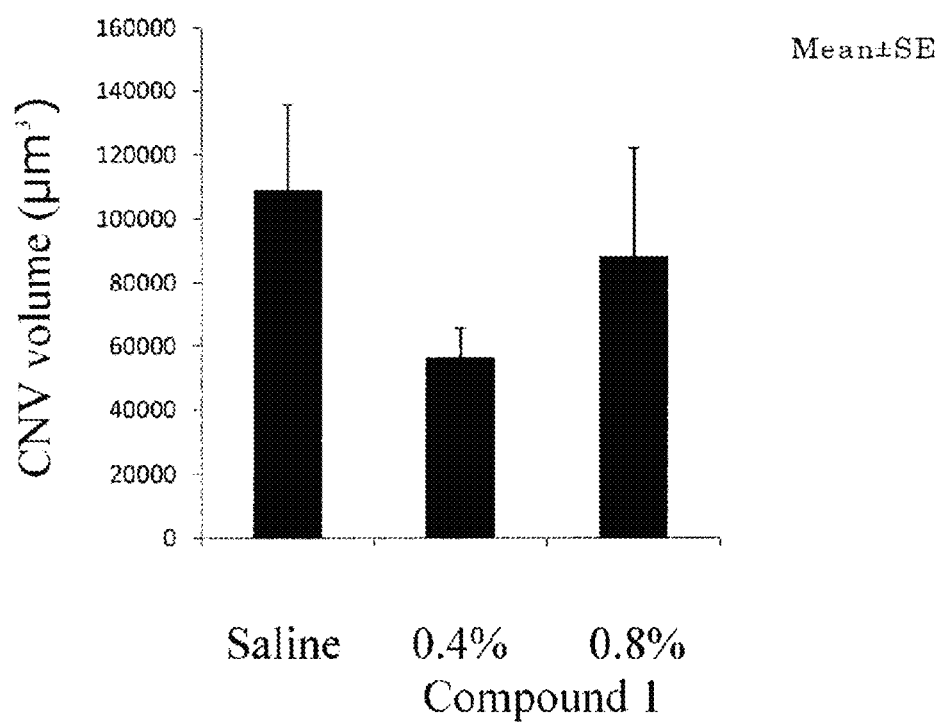
FIG. 9 is a graph showing the result of quantification of choroidal neovascularization volume of each of the instillation groups by fluorescein fundus angiography. The vertical axis of the graph represents the volume of choroidal neovascularization ($\mu m^3$) and values are represented as mean±standard error.

The results of the test are shown in FIG. 9. As can be seen from FIG. 9, the CNV volume of the control group (Control) was 109177±26399 $\mu m^3$, whereas the CNV volume of the 0.4% compound 1 solution instillation group was 56408±9007 $\mu m^3$, the CNV volume of the 0.8% compound 1 solution instillation group was 88387±33678 $\mu m^3$, that is, choroidal neovascularization was suppressed.

Example 3

Effects in Kimba Mice

The effectiveness of the compound 1 in Kimba (trVEGF029) mice known as mice transgenic for VEGF gene, which develop retinal neovascularization, was examined in the following manner.

1. Test Method

A. Drugs and Animals Used in Test

Compound 1 solution prepared in the same manner as in Example 1: 0.8% solution (instillation volume: 20 μL)

Test animals: Kimba mice (available from Lions Eye Institute Ltd., 6 mice per group)

B. Drug Administration Method and Evaluation Method

One-month-old Kimba mice born on the same day were given saline (control) or the 0.8% compound 1 solution by ocular instillation three times a day for 2 weeks, and were then subjected to fluorescein fundus angiography and optical coherence tomography under anesthesia for evaluation. More specifically, in fluorescein fundus angiography, each of the mice was first given tropicamide by ocular instillation to cause mydriasis and then anesthetized by intraperitoneal administration of 100 mg/kg of Ketalar and 10 mg/kg of Selactar, given 6 μL/g of a contrast agent for fluorescein fundus angiography by intraperitoneal injection, and subjected to fluorescein fundus angiography using Heidelberg Retina Angiograph (HRA, Heidelberg, Germany). Further, in evaluation by optical coherence tomography, each of the mice was given tropicamide by ocular instillation to cause mydriasis, anesthetized by intraperitoneal administration of 100 mg/kg of Ketalar and 10 mg/kg of Selactar, and subjected to imaging with The Cirrus HD-OCT (Carl Zeiss Meditec, Dublin, Calif.) by 5-line scan (scan length: 6 mm) in X and Y axis directions to measure an average maximum retinal thickness (statistical analysis was performed by Student's t test).

2. Results and Discussion

Figure 10:
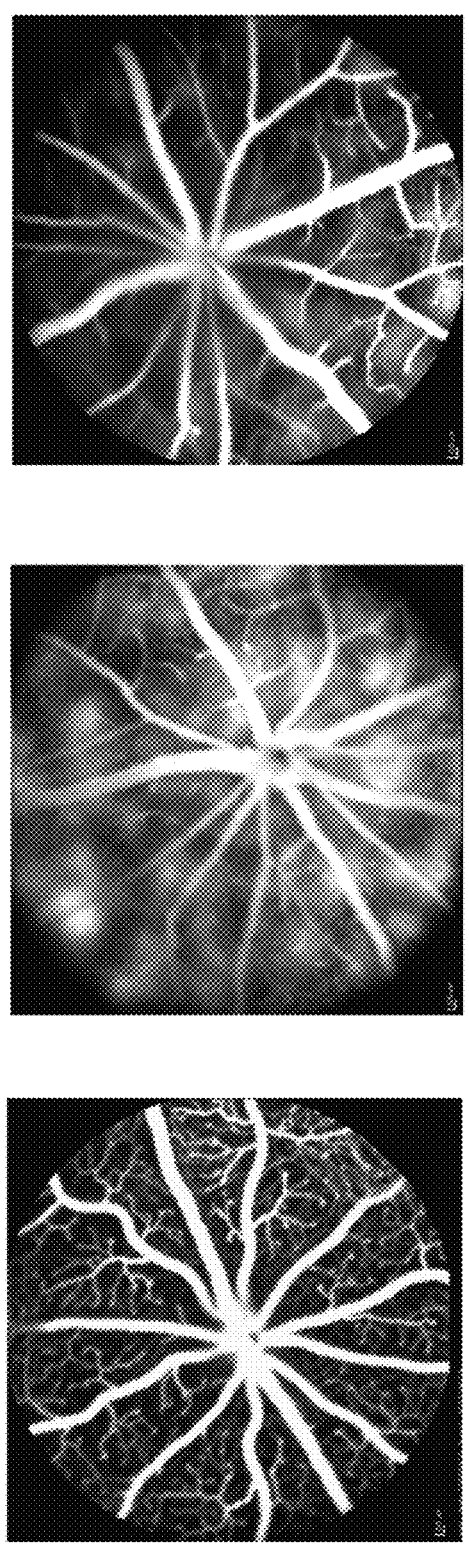
FIG. 10 shows representative fluorescein fundus angiography and optical coherence tomography images of a normal mouse (reference), a saline instillation group (control), and a 0.8% compound 1 solution instillation group.
Figure 10:
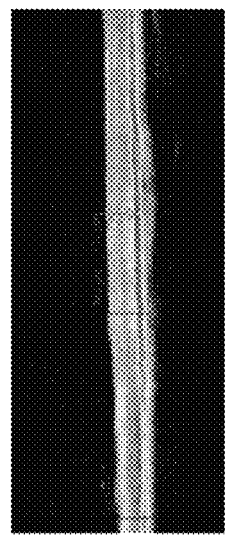
Figure 10:
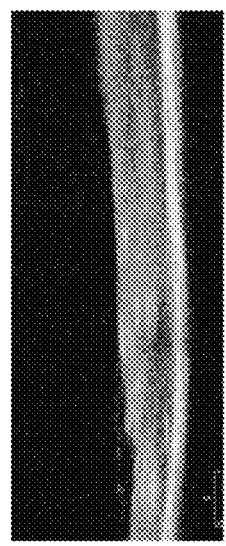
Figure 10:
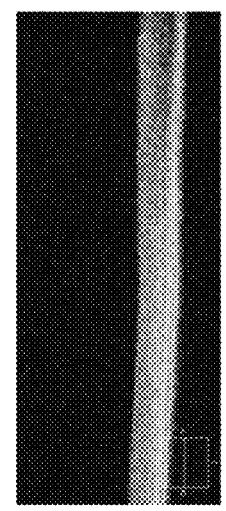
Figure 11:
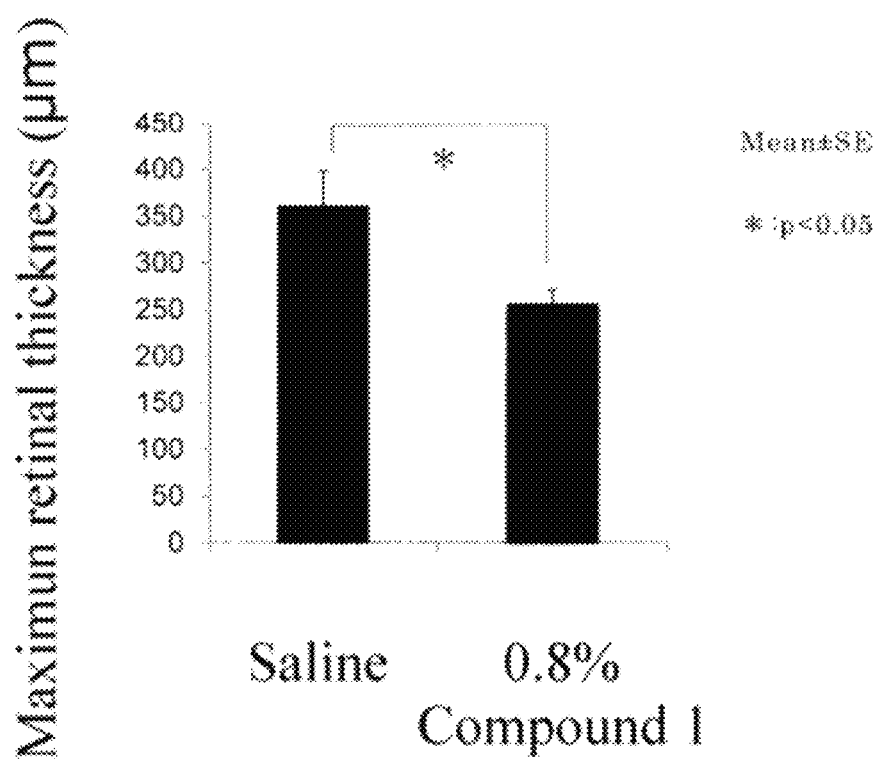
FIG. 11 is a graph showing the maximum retinal thickness (mean±standard error, unit: $\mu m$) of each of the instillation groups measured by optical coherence tomography, wherein * indicates that p-value is less than 0.05.

The results of the test are shown in FIGS. 10 and 11. In FIG. 10, the upper images are representative fluorescein fundus angiography images of the test groups and the lower images are representative optical coherence tomography images of the test groups. It is to be noted that fluorescein fundus angiography and optical coherence tomography images of a normal mouse are also shown as a reference example (left side, maximum retinal thickness of this example: 276 μm). As can be seen from FIG. 10, in the case of saline instillation, edema is observed and retinal thickening is also observed, whereas in the case of 0.8% compound 1 solution instillation, suppression of edema is observed and the retina is comparable in thickness to that of the normal mouse. FIG. 11 is a graph showing the values of retinal thickness. As can be seen from FIG. 11, the average maximum retinal thickness of the saline instillation group (control) was 361.8±36.1 μm, whereas the average maximum retinal thickness of the 0.8% compound 1 solution instillation group was 256.7±35.7 μm, that is, retinal thickening was significantly suppressed.

Example 4

Effects on Tight Junction

The effectiveness of the compound 1 on intercellular barriers was examined in the following manner.

1. Test Method

According to a conventional method, b-END3 (bEND.3: ATCC CRL-2299 ™) cells, which are mouse brain microvascular endothelial cells, were subcultured in 3.5 cm dishes ($9 \times 10^5$ cells/dish), and a test was started from day 6 after subculture. The cells were subjected to drug treatment under the following five or six conditions: no treatment (shown in FIGS. 12 and 13 as "control"); VEGF stimulation (25 ng/mL, 24 hours) (shown in FIGS. 12 and 13 as "VEGF (25 ng/mL 24 hours) stimulation"); pretreatment with the compound 1 (3 μM or 30 μM, 3 hours) followed by VEGF stimulation (25 ng/mL, 24 hours) (shown in FIGS. 12 and 13 as "VEGF+Compound 1 (3 μM 3 hours) pretreatment" or "VEGF+Compound 1 (30 μM 3 hours) pretreatment"); IL-6 stimulation (10 ng/mL, 24 hours) (shown in FIGS. 12 and 13 as "IL-6 (10 ng/mL 24 hours) stimulation"); and pretreatment with the compound 1 (30 μM, 3 hours) followed by IL-6 stimulation (10 ng/mL, 24 hours) (shown in FIGS. 12 and 13 as "IL-6+Compound 1 (30 μM 3 hours) pretreatment").

The cells after the test were subjected to immunostaining according to the following procedure to evaluate the expression of Claudin-5 or F-Actin. More specifically, the cells after the test were treated with 100% methanol at ordinary temperature for 5 minutes, further treated with 50% methanol for 5 minutes, and washed with PBS twice (5 min per wash). Then, a cover glass-sized cell sample was prepared by trimming with a cotton swab, enclosed with a Dako pen, blocked with 10% normal goat serum (10% normal goat serum ready-to-use (Invitrogen)) (30 min, ordinary temperature), and allowed to stand at 4° C. overnight. Then, the cell sample was subjected to primary antibody treatment by dropping 50 to 70 μL of a 25-fold dilution of rabbit anti-claudin-5 antibody (Rabbit anti-Claudin-5 (Invitrogen 34-1600)) or rabbit anti-F-actin antibody (Rabbit anti-F-actin (Biossusa bs-1571R)) and then washing with PBS three times (10 min per wash). Then, the cell sample was allowed to stand at ordinary temperature for 60 minutes under dark conditions, and was then subjected to secondary antibody treatment with a 200-fold dilution of anti-rabbit IgG FITC labeled with Alexa Fluo488™ (Alexa Fluo488 anti-Rabbit IgG FITC) and washed with PBS three times (10 min per wash). Then, the cell sample was subjected to nuclear staining with DAPI and covered with Crystal Mount as a cover glass, and then its image was taken with a microscope (400× magnification). The results for Claudin-5 are shown in FIG. 12 and the results for F-actin are shown in FIG. 13.

2. Results and Discussion

Figure 12:
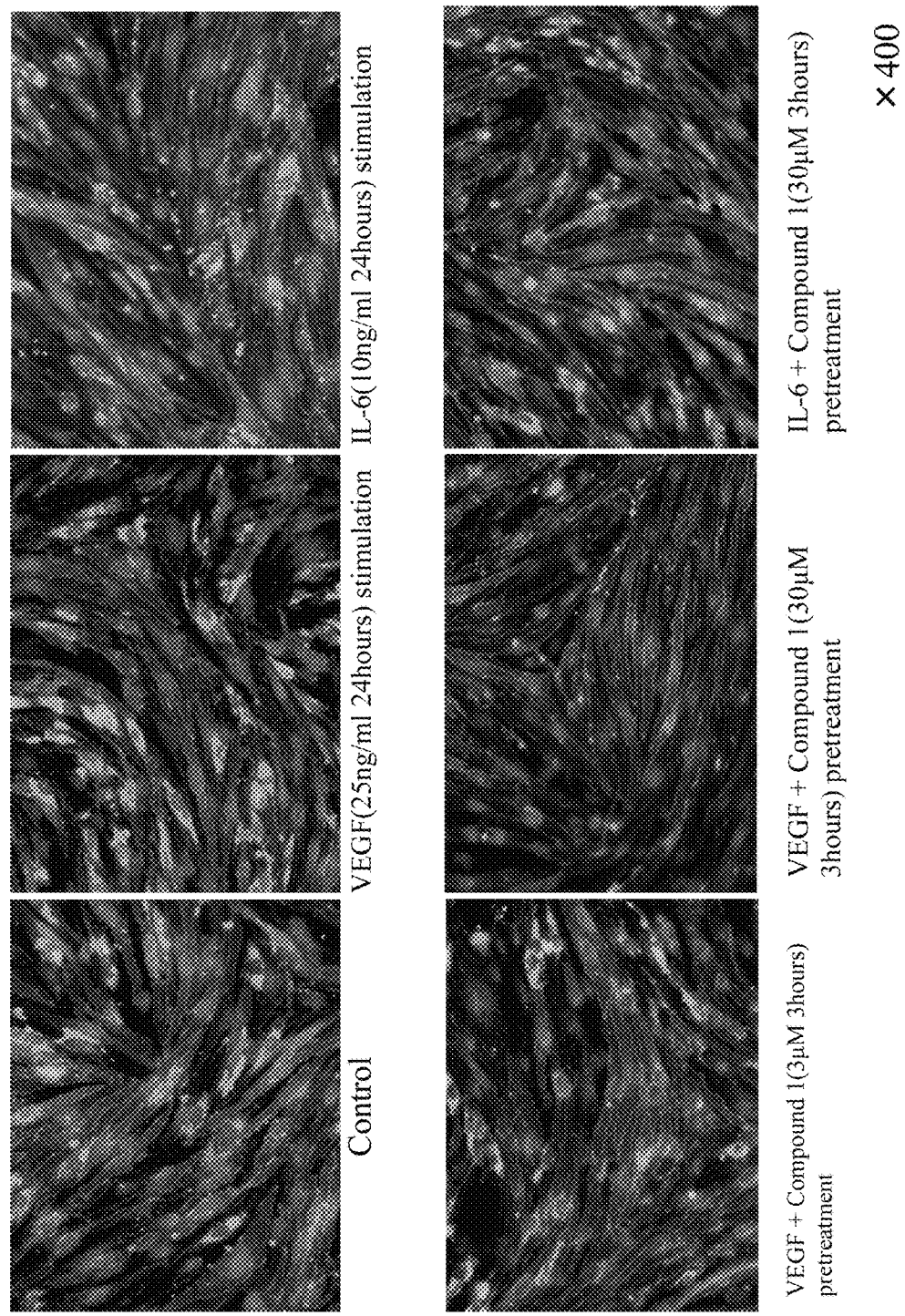
FIG. 12 shows immunostaining images that demonstrate the effect of the compound 1 on Claudin-5 expression by VEGF stimulation or IL-6 stimulation.
Figure 13:
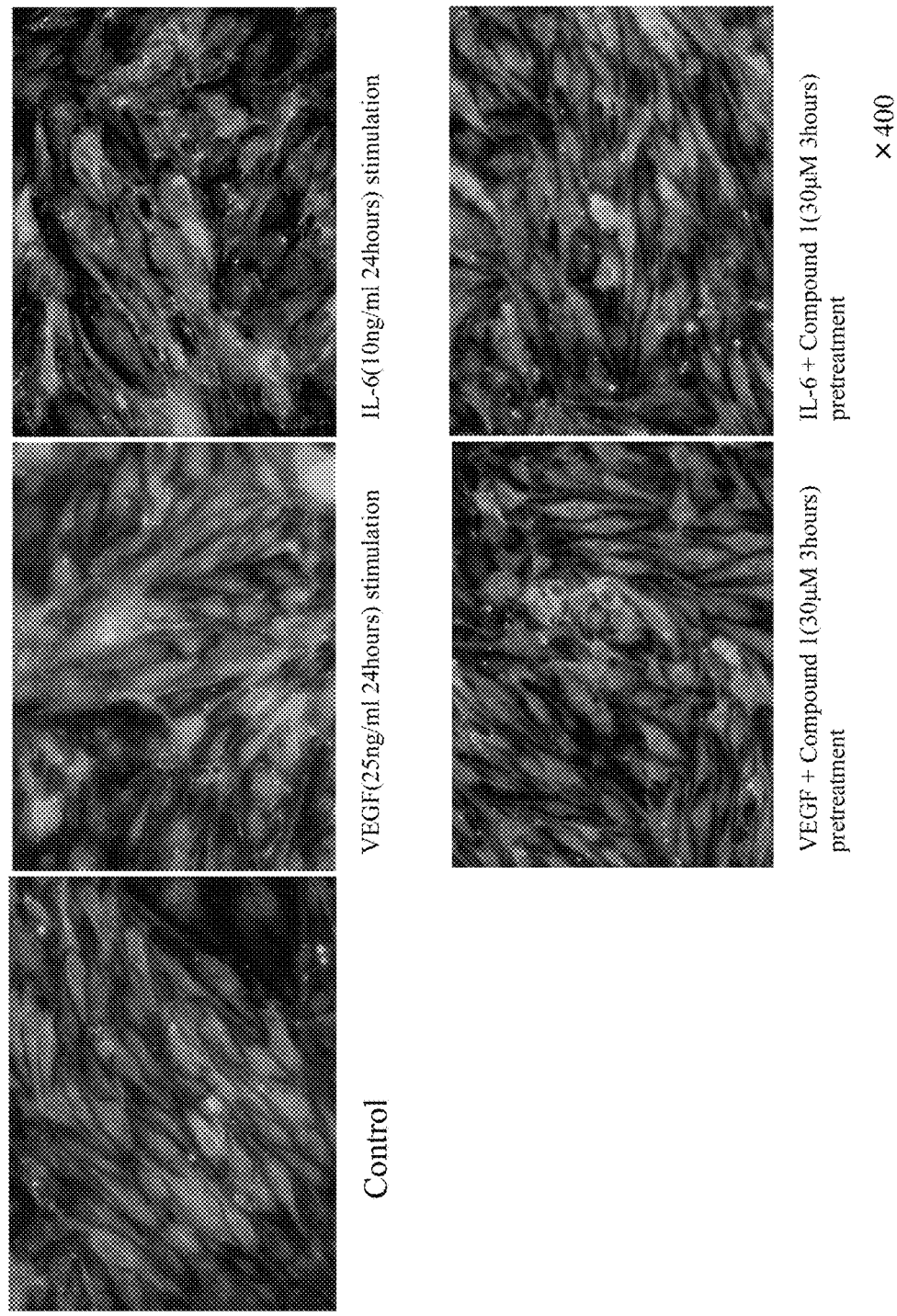
FIG. 13 shows immunostaining images that demonstrate the effect of the compound 1 on F-Actin polymerization that is caused by VEGF stimulation or IL-6 stimulation.

The results of immunostaining for Claudin-5 are shown in FIG. 12 and the results of immunostaining for F-Actin are shown in FIG. 13. As can be seen from FIG. 12, improvement in Claudin-5 expression, which is decreased by VEGF stimulation or IL-6 stimulation, by pretreatment with the compound 1 is observed. Further, as can be seen from FIG. 13, suppression of F-Actin polymerization, which is caused by VEGF stimulation or IL-6 stimulation, by pretreatment with the compound 1 is observed. These results indicate that the compound 1 is expected to have the effect of suppressing the breakdown of intercellular barriers.

INDUSTRIAL APPLICABILITY (S)-(−)-1-(4-fluoro-5-isoquinolinesulfonyl)-2-methyl-1,4-homopiperazine, a salt thereof, or a solvate thereof used in the present invention has an excellent neovascularization suppression effect, and is therefore useful as a drug for preventing or treating ocular fundus disease, especially diabetic retinopathy or age-related macular degeneration.

What is claimed is:

1. A method of treating ocular fundus disease comprising: administering an effective amount of an agent comprising (S)-(−)-1-(4-fluoro-5-isoquinolinesulfonyl)-2-methyl-1,4-homopiperazine, a salt thereof, or a solvate thereof to a subject in need thereof,
wherein the ocular fundus disease is a diabetic macular edema or exudative age-related macular degeneration.

2. The method according to claim 1, wherein the ocular fundus disease is diabetic macular edema.

3. The method according to claim 1, wherein the ocular fundus disease is exudative age-related macular degeneration.

4. The method according to claim 1, wherein the agent is an ophthalmic preparation.

5. The method according to claim 1, wherein administration of the agent is performed by ocular instillation.

6. The method according to claim 2, wherein administration of the agent is performed by ocular instillation.

7. The method according to claim 3, wherein administration of the agent is performed by ocular instillation.

* * * * *